US011133099B2

(12) United States Patent
Kline et al.

(10) Patent No.: US 11,133,099 B2
(45) Date of Patent: Sep. 28, 2021

(54) MEMORY RECALL ASSISTANCE FOR MEMORY LOSS

(71) Applicant: International Business Machines Corporation, Armonk, NY (US)

(72) Inventors: Eric V. Kline, Rochester, MN (US); Sarbajit K. Rakshit, Kolkata (IN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 279 days.

(21) Appl. No.: 16/034,590

(22) Filed: Jul. 13, 2018

(65) Prior Publication Data

US 2020/0020433 A1   Jan. 16, 2020

(51) Int. Cl.
  *G16H 20/70* (2018.01)
  *G06F 16/16* (2019.01)
(52) U.S. Cl.
  CPC .......... *G16H 20/70* (2018.01); *G06F 16/164* (2019.01)
(58) Field of Classification Search
  CPC .............................. G16H 20/70; G06F 16/164
  See application file for complete search history.

(56) References Cited

U.S. PATENT DOCUMENTS

| 6,549,915 | B2 * | 4/2003 | Abbott, III | G06F 16/40 |
| 6,950,026 | B2 * | 9/2005 | Yamashita | G06Q 10/10 340/539.22 |
| 7,162,473 | B2 * | 1/2007 | Dumais | G06F 16/9535 |
| 7,702,599 | B2 * | 4/2010 | Widrow | G06K 9/6247 706/26 |
| 9,451,899 | B2 * | 9/2016 | Ritchey | A61B 5/369 |
| 9,711,056 | B1 * | 7/2017 | Nguyen | G09B 5/02 |
| 9,747,902 | B2 * | 8/2017 | Jasinschi | G10L 25/66 |
| 10,127,825 | B1 * | 11/2018 | Nguyen | G10L 15/26 |
| 2002/0032689 | A1 * | 3/2002 | Abbott, III | G06F 16/907 |
| 2009/0102913 | A1 |  4/2009 | Jaffres et al. | |

(Continued)

FOREIGN PATENT DOCUMENTS

WO    01/86464 A1    11/2001

OTHER PUBLICATIONS

Graus et al.; "Analyzing and Predicting Task Reminders"; Microsoft Research Paper (2016); 9 pages; <https://www.microsoft.com/en-us/research/wp-content/uploads/2016/11/Cortana-reminders_UM_2016.pdf>.

(Continued)

*Primary Examiner* — Malina D. Blaise
(74) *Attorney, Agent, or Firm* — Cantor Colburn LLP; Tihon Poltavets

(57) ABSTRACT

Provided are systems, methods, and media for assisting recall of a lost memory. An example method includes receiving activity data and associated metadata regarding a plurality of activities participated in by a user over a plurality of time periods. The method includes generating a memory chain graph that spans the plurality of time periods, in which the graph includes a plurality of memory events and a plurality of memory pointers. The method includes identifying a memory event of the memory chain graph that the user is unable to presently recall, selecting a memory pointer that is linked to the memory event, and then presenting the user with information corresponding to the selected memory pointer to assist the user in recalling the memory event.

17 Claims, 6 Drawing Sheets

(56) References Cited

U.S. PATENT DOCUMENTS

| | | | | |
|---|---|---|---|---|
| 2010/0041958 A1* | 2/2010 | Leuthardt | ............. | G16H 20/10 |
| | | | | 600/300 |
| 2010/0125561 A1* | 5/2010 | Leuthardt | ............. | G16H 20/70 |
| | | | | 707/706 |
| 2011/0196923 A1 | 8/2011 | Marcucci et al. | | |
| 2014/0297642 A1* | 10/2014 | Lum | .................... | G06F 16/287 |
| | | | | 707/737 |
| 2017/0319063 A1* | 11/2017 | Verdooner | ........... | A61B 5/4809 |
| 2018/0239767 A1* | 8/2018 | Bostick | .............. | G06F 16/4393 |

OTHER PUBLICATIONS

Jeans; "Anamnesis"; A Project Presented to the Faculty of San Diego State University (2011); 42 pages.
Mell et al.; "The NIST Definition of Cloud Computing- Recommendations of the National Institute of Standards and Technology"; US Department of Commerce; Sep. 2011; 7 pages.

\* cited by examiner

MEMORY RECALL ASSISTANCE FOR MEMORY LOSS

BACKGROUND

The present invention generally relates to the field of patient assistance devices, and more specifically, to systems and methods for memory recall assistance for a memory loss.

People often have issues recalling certain incidents, persons, or places that the person was involved in at a given point in time. Memory loss can occur for various reasons. For example, a person may be suffering from memory loss as a result of an accident, cerebral stroke, Dementia, Alzheimer's disease, or other events that cause mental impairments. Patients in a hospital for example, may have certain mental conditions that cause the patient to forget activities that the patient was previously involved in or people that the patient previously recognized.

One technique utilized by people to attempt to recollect a forgotten content memory is to search for other reference points that the person is able to recall so that any correlation with the forgotten content may be identified and accordingly the forgotten content recalled. For example if a user, such as a patient, is not able to recall the name of a person but is able to remember a location that the user visited with the person, the user may search and attempt to recall other pointers associated with the forgotten person so that user is better able to recall the name of the person.

SUMMARY

Embodiments of the present invention are directed to a computer-implemented method for assisting recall of a lost memory of a user. A non-limiting example of the computer-implemented method includes receiving, by a system comprising one or more processors, activity data and associated metadata regarding a plurality of activities participated in by a user over a plurality of time periods. The method includes generating, by the system, a memory chain that spans the plurality of time periods, in which the memory chain is generated based on the activity data and associated metadata. The memory chain includes a plurality of memory events and a plurality of memory pointers, in which each memory event of the plurality of memory events is linked to at least one other event of the plurality of events via a memory pointer of the plurality of memory pointers. The method includes identifying, by the system, a memory event of the memory chain that the user is unable to presently recall. The method includes selecting, by the system, a memory pointer that is linked to the memory event and presenting the user with information corresponding to the selected memory pointer to assist the user in recalling the memory event.

Embodiments of the present invention are directed to a system for assisting recall of a lost memory of a user. The system includes one or more processors that are configured to perform a method. A non-limiting example of the method includes receiving, by the system, activity data and associated metadata regarding a plurality of activities participated in by a user over a plurality of time periods. The method includes generating, by the system, a memory chain that spans the plurality of time periods, in which the memory chain is generated based on the activity data and associated metadata. The memory chain includes a plurality of memory events and a plurality of memory pointers, in which each memory event of the plurality of memory events is linked to at least one other event of the plurality of events via a memory pointer of the plurality of memory pointers. The method includes identifying, by the system, a memory event of the memory chain that the user is unable to presently recall. The method includes selecting, by the system, a memory pointer that is linked to the memory event and presenting the user with information corresponding to the selected memory pointer to assist the user in recalling the memory event.

Embodiments of the invention are directed to a computer program product for assisting recall of a lost memory of a user, the computer program product comprising a computer readable storage medium having program instructions embodied therewith. The program instructions are executable by a processor to cause the processor to perform a method. A non-limiting example of the method includes receiving, by the system, activity data and associated metadata regarding a plurality of activities participated in by a user over a plurality of time periods. The method includes generating, by the system, a memory chain that spans the plurality of time periods, in which the memory chain is generated based on the activity data and associated metadata. The memory chain includes a plurality of memory events and a plurality of memory pointers, in which each memory event of the plurality of memory events is linked to at least one other event of the plurality of events via a memory pointer of the plurality of memory pointers. The method includes identifying, by the system, a memory event of the memory chain that the user is unable to presently recall. The method includes selecting, by the system, a memory pointer that is linked to the memory event and presenting the user with information corresponding to the selected memory pointer to assist the user in recalling the memory event.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

Figure 1:
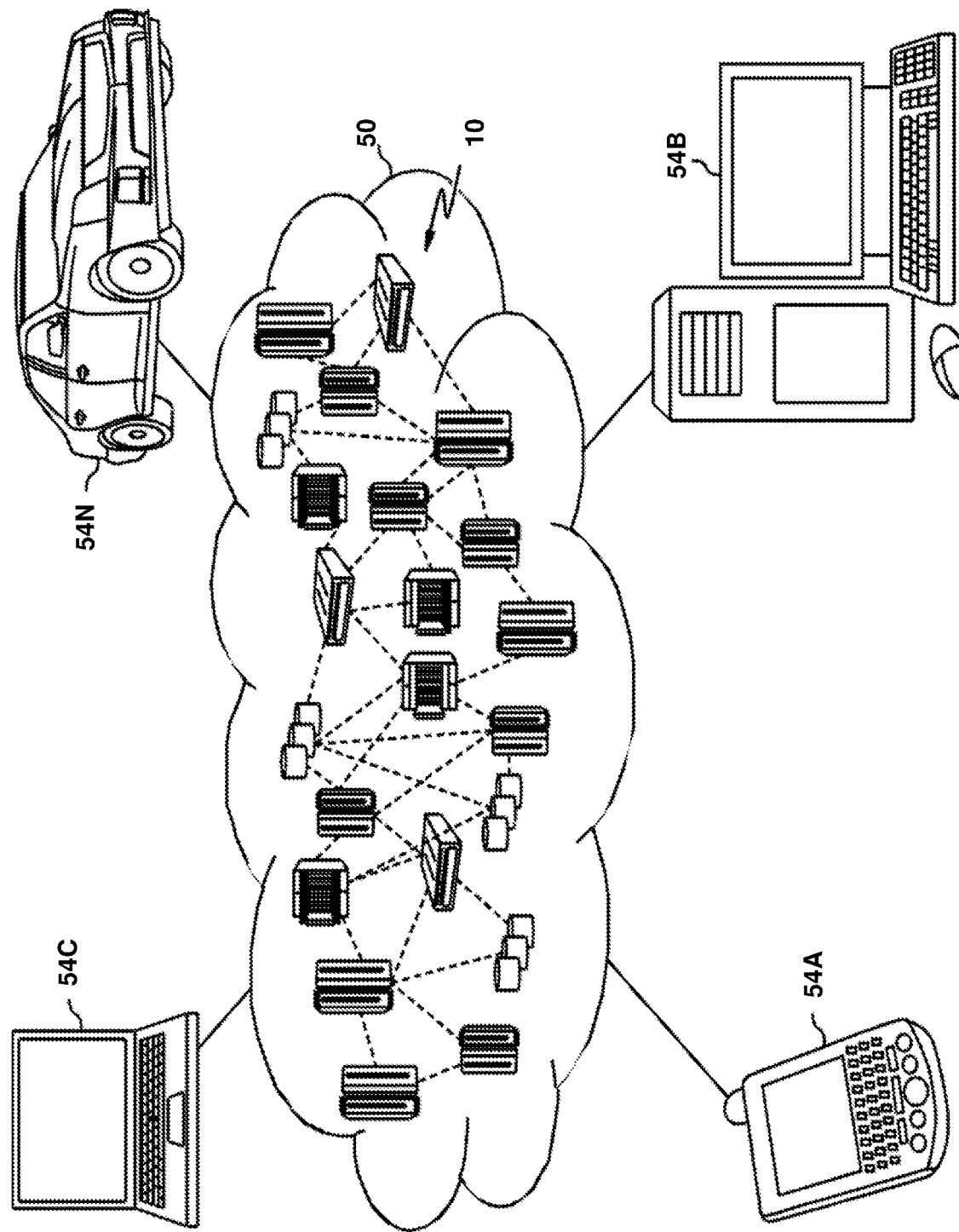
FIG. 1 depicts a cloud computing environment according to one or more embodiments of the present invention.

The diagrams depicted herein are illustrative. There can be many variations to the diagram or the operations described therein without departing from the spirit of the invention. For instance, the actions can be performed in a differing order or actions can be added, deleted, or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the disclosed embodiments, the various elements illustrated in the figures are provided with two-digit or three-digit reference numbers. With minor exceptions (e.g., FIGS. 1-2), the leftmost digit(s) of each reference number correspond to the figure in which its element is first illustrated.

DETAILED DESCRIPTION

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" may be understood to include any integer number greater than or equal to one, i.e. one, two, three, four, etc. The terms "a plurality" may be understood to include any integer number greater than or equal to two, i.e. two, three, four, five, etc. The term "connection" may include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems; storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 1, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms, and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
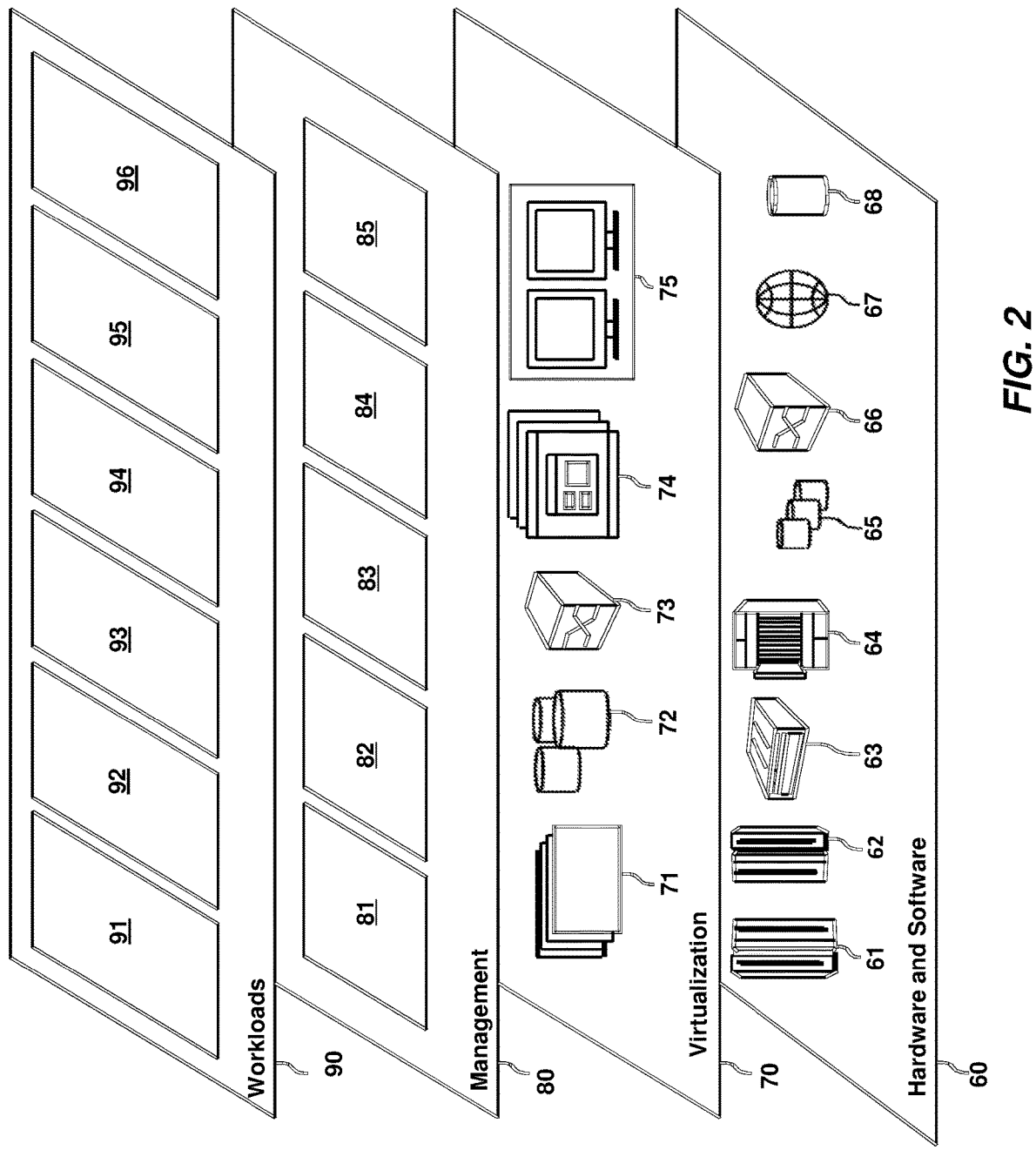
FIG. 2 depicts abstraction model layers according to one or more embodiments of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and memory recall processing 96.

Turning now to an overview of technologies that are more specifically relevant to aspects of the invention, as noted above, people often have issues recalling certain incidents, persons, or places that the person was involved in at a given point in time. Memory loss can occur for various reasons. For example, a person may suffering from memory loss as a result of an accident, cerebral stroke, Dementia, Alzheimer's disease, other events that cause mental impairments.

Some known systems attempt to assist a patient having memory loss by providing behavioral support information in response to detecting a lost memory. However those systems do not select between particular memory pointers to guide a user through a particular memory loss pattern, nor do those systems analyze biometric or visual signals of a user after providing memory content of a particular memory pointer, or then guide the user to a particular second memory pointer based on the results of the analysis.

Turning now to an overview of the aspects of the invention, one or more embodiments of the invention address the above-described shortcomings of the prior art by providing a computing system that is configured to generate a memory chain that spans a plurality of time periods, identify a memory event of the memory chain that the user is unable to presently recall, select a memory pointer that is linked to the memory event in the memory chain in response to identifying a memory event that the user is unable to presently recall, and then present the user with information corresponding to the selected memory pointer to assist the user in recalling the memory event (e.g., associated image objects, photographs, audio contents, textual contents, etc.). In some embodiments of the present invention, the memory chain comprises a graphical representation (i.e., a memory chain graph). In some embodiments of the present invention, biometric and/or visual signals of the user are analyzed to track the effectiveness of the provided information and/or to identify a memory event that the user is unable to presently recall. Based on the effectiveness of the provided information corresponded to the selected memory pointer, one or more secondary pointers are then dynamically selected and content information, associated with the secondary pointers, is provided to the user.

The above-described aspects of the invention address the shortcomings of the prior art by providing a system that is capable of identifying which portion of a memory of a user, such as a patient, is completely or partially lost in a particular time scale (e.g., lost childhood memory), and providing various memory pointers to assist the user in recalling the lost memory, in which the memory recall pointers are identified by the system in such a way that the patient is able to create a present correlation with the lost memory.

Figure 3:
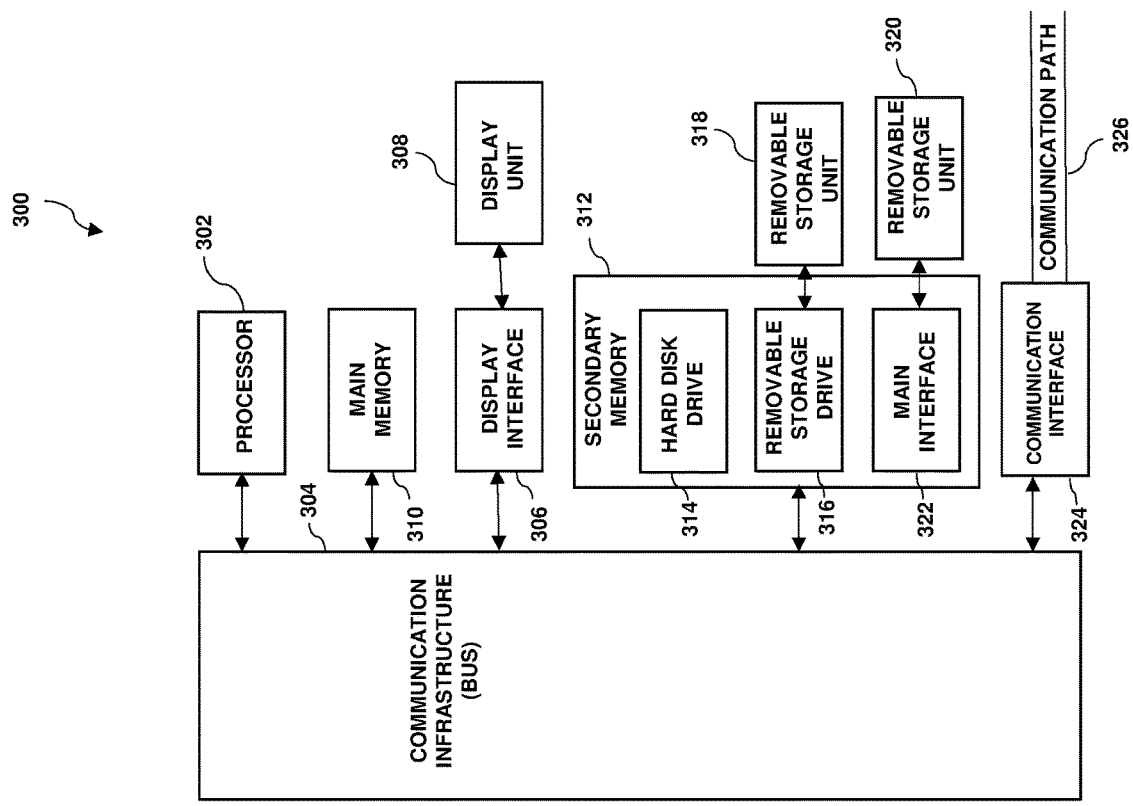
FIG. 3 depicts an exemplary computer system capable of implementing one or more embodiments of the present invention.

Turning now to a more detailed description of aspects of the present invention, FIG. 3 illustrates a high-level block diagram showing an example of a computer-based system 300 that is useful for implementing one or more embodiments of the invention. Although one exemplary computer system 300 is shown, computer system 300 includes a communication path 326, which connects computer system 300 to additional systems and may include one or more wide area networks (WANs) and/or local area networks (LANs) such as the internet, intranet(s), and/or wireless communication network(s). Computer system 300 and additional systems are in communication via communication path 326, (e.g., to communicate data between them).

Computer system 300 includes one or more processors, such as processor 302. Processor 302 is connected to a communication infrastructure 304 (e.g., a communications bus, cross-over bar, or network). Computer system 300 can include a display interface 306 that forwards graphics, text, and other data from communication infrastructure 304 (or from a frame buffer not shown) for display on a display unit 308. Computer system 300 also includes a main memory 310, preferably random access memory (RAM), and may also include a secondary memory 312. Secondary memory 312 may include, for example, a hard disk drive 314 and/or a removable storage drive 316, representing, for example, a floppy disk drive, a magnetic tape drive, or an optical disk drive. Removable storage drive 316 reads from and/or writes to a removable storage unit 318 in a manner well known to those having ordinary skill in the art. Removable storage unit 318 represents, for example, a floppy disk, a compact disc, a magnetic tape, or an optical disk, etc., which is read by and written to by a removable storage drive 316. As will be appreciated, removable storage unit 318 includes a computer readable medium having stored therein computer software and/or data.

In some alternative embodiments of the invention, secondary memory 312 may include other similar means for allowing computer programs or other instructions to be loaded into the computer system. Such means may include, for example, a removable storage unit 320 and an interface 322. Examples of such means may include a program package and package interface (such as that found in video game devices), a removable memory chip (such as an EPROM or PROM) and associated socket, and other removable storage units 320 and interfaces 322 which allow software and data to be transferred from the removable storage unit 320 to computer system 300.

Computer system 300 may also include a communications interface 324. Communications interface 324 allows software and data to be transferred between the computer system and external devices. Examples of communications interface 324 may include a modem, a network interface (such as an Ethernet card), a communications port, or a PCM-CIA slot and card, etc. Software and data transferred via communications interface 324 are in the form of signals which may be, for example, electronic, electromagnetic, optical, or other signals capable of being received by communications interface 324. These signals are provided to communications interface 324 via communication path (i.e., channel) 326. Communication path 326 carries signals and may be implemented using a wire or cable, fiber optics, a phone line, a cellular phone link, an RF link, and/or other communications channels.

In the present disclosure, the terms "computer program medium," "computer usable medium," and "computer readable medium" are used to generally refer to media such as main memory 310 and secondary memory 312, removable storage drive 316, and a hard disk installed in hard disk drive 314. Computer programs (also called computer control logic) are stored in main memory 310, and/or secondary memory 312. Computer programs may also be received via communications interface 324. Such computer programs, when run, enable the computer system to perform the features of the present disclosure as discussed herein. In particular, the computer programs, when run, enable processor 302 to perform the features of the computer system. Accordingly, such computer programs represent controllers of the computer system.

Figure 4:
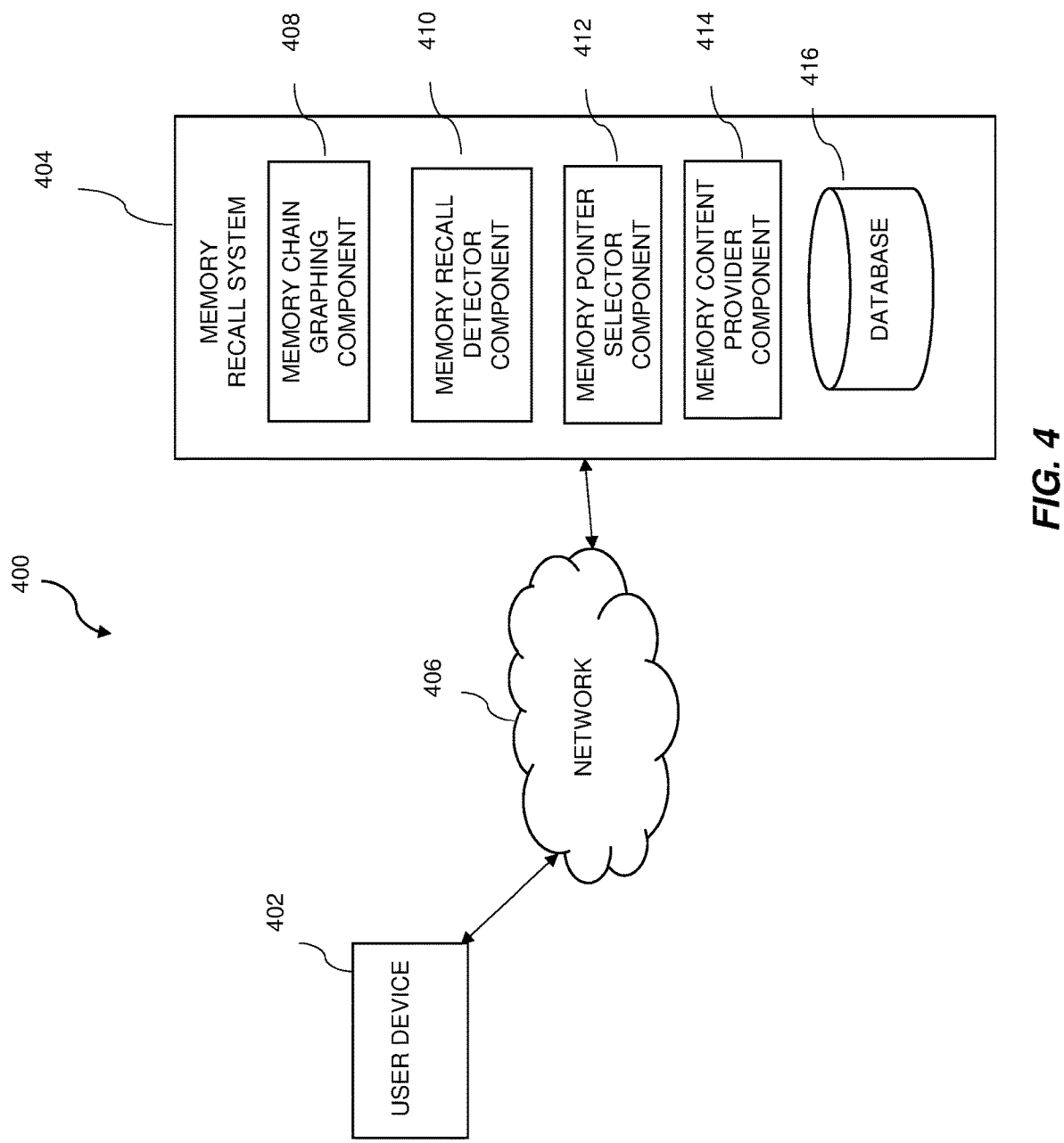
FIG. 4 depicts an example distributed environment in accordance with one or more embodiments of the present invention.

Referring now to FIG. 4, an example distributed environment 400 is presented for assisting recall of a lost memory. Distributed environment 400 includes user device 402 and a memory recall system 404, which are interconnected via network 406. FIG. 4 provides an illustration of only one example system and does not imply any limitation with regard to other systems in which different embodiments of the present invention may be implemented. Various suitable modifications to the depicted environment may be made, by those skilled in the art, without departing from the scope of the invention as recited by the claims.

Memory recall system 404 includes a memory chain graphing component 408, memory recall detector component 410, memory pointer selector component 412, memory content provider component 414, and database 416. In some embodiments of the present invention, memory chain graphing component 408, memory recall detector component 410, memory pointer selector component 412, and/or memory content provider component 414, are interconnected via a communication infrastructure 304 and/or communication path 326. Memory recall system 404 may have internal and external hardware components, such as those depicted and described above with respect to FIG. 3.

In general, memory recall system 404 is configured to receive activity data and associated metadata regarding a plurality of activities participated in by a user over a plurality of time periods, generate a memory chain (e.g., a memory chain graph) that spans the plurality of time periods, identify a memory event of the memory chain that the user is unable to presently recall, and in response to identifying a memory event that the user is unable to presently recall, then select a memory pointer that is linked to the memory event and present the user with information corresponding to the selected memory pointer to assist the user in recalling the memory event.

In some embodiments of the present invention, memory recall system 404 is a standalone computing device, a management server, a web server, a mobile computing device, or other suitable electronic device and/or computing system capable of receiving, sending, and processing data. In some embodiments of the present invention, memory recall system 404 is a server computing system utilizing multiple computers, such as in cloud computing environment 50. In some embodiments of the present invention, memory recall system 404 is a laptop computer, a tablet computer, a netbook computer, a personal computer (PC), a desktop computer, a personal digital assistant (PDA), a smart phone, or other suitable programmable electronic device capable of communicating with user device 402 and other computing devices (not shown) within distributed environment 400 via network 406. In some embodiments of the present invention, memory recall system 404 is a computing system utilizing clustered computers and components (e.g., database server computers, application server computers, etc.) that act as a single pool of seamless resources that are accessible within distributed environment 400. Memory recall system 404 may have internal and external hardware components, such as those depicted and described above with respect to FIG. 3.

Network 406 can be, for example, a telecommunications network, a local area network (LAN), a wide area network (WAN), such as the Internet, or a combination of the three, and can include wired, wireless, or fiber optic connections. Network 406 can include one or more wired and/or wireless networks that are capable of receiving and transmitting data, voice, and/or video signals, including multimedia signals that include voice, data, and video information. In general, network 406 can be any suitable combination of connections and protocols that can support communications between user device 402, memory recall system 404, and/or other computing devices (not shown) within a distributed environment 400. In some embodiments of the present invention, distributed environment 400 is implemented as part of a cloud computing environment such as cloud computing environment 50 (FIG. 1).

User device 402 is configured to allow users to send and/or receive information from user device 402 to memory recall system 404, which in turn allows users to access memory chain graphing component 408, memory recall detector component 410, memory pointer selector component 412, and/or memory content provider component 414. In some embodiments of the present invention, user device 402 is configured to gather day to day activity of the user along with associated metadata of the activity (e.g., location, timing, weather conditions, participants who are associated with the user, biometric data, visual data, etc.). For example, in some embodiment of the present invention, user device 402 includes one or more sensors for obtaining sensor data of the user. For example, in some embodiments of the present invention, user device 402 includes a GPS device that is configured to obtain location information of the user device, which may be used to determine a movement pattern of the user. In some embodiments of the present invention, user device 402 is configured to capture audio, images, and/or video of an activity of the user (e.g., via a microphone and/or camera of user device 402).

In some embodiments of the present invention, user device 402 is configured to share behavior information relating to the user's activity. For example, in some embodiments of the present invention, user device 402 is configured to detect what programs the user watches on a given day and/or audio content that is listened to by the user in a given day. In some embodiments of the present invention, one or more of the activity data and the associated metadata is provided by the user via a user input interface of user device 402. For example, in some embodiments of the present invention, a user may enter a date, time, the names of people, an activity performed, and/or any other type of event data relating to an event that a user is participating in or has participated in.

In some embodiments of the present invention, user device 402 is a laptop computer, a tablet computer, a netbook computer, a personal computer (PC), a desktop computer, a personal digital assistant (PDA), a smart phone, or other suitable programmable electronic device capable of communicating with various components and devices within distributed environment 400. In some embodiments of the present invention, user device 402 is a programmable electronic mobile device or a combination of programmable electronic mobile devices capable of executing machine readable program instructions and communicating with other computing devices (not shown) within distributed environment 400. In some embodiments of the present invention, user device 402 may include internal and external hardware components, such as those depicted and described above with respect to FIG. 3.

As noted above, memory recall system 404 is configured to receive activity data and associated metadata regarding a plurality of activities participated in by a user over a plurality of time periods. In some embodiments of the present invention, the activity data and/or the associated metadata is obtained from user device 402. In some embodiments of the present invention, the activity data and/or the associated metadata is obtained from other additional or alternative sources besides user device 402. For example, in some embodiments of the present invention, the activity data and/or the associated metadata is from a social network site and/or social media application.

Memory recall system 404 is configured to analyze the received activity data and associated metadata and generate a memory chain (e.g., memory chain graph) that spans the plurality of time periods based on the activity data and the associated metadata (e.g., via memory chain graphing component 408). As will be discussed in more detail below in regards to FIG. 5, in some embodiments of the present invention, the generated memory chain comprises a directed graph having nodes connected by edges, in which a subset of nodes represent a set of memory events and in which a subset of the edges represents an asset of memory pointers. In some embodiments of the present invention, the generated memory chain includes a plurality of memory events and a plurality of memory pointers, in which the memory event and memory pointers span a plurality of time periods (e.g., years, months, days, hours, etc.). In the generated memory chain, each memory event of the plurality of memory events may be linked to at least one other event of the plurality of events via a memory pointer of the plurality of memory pointers. In some embodiments of the present invention, each memory event of the plurality of memory events represents a particular activity that the user participated in at a certain time. In some embodiments of the present invention, memory recall system 404 generates the memory chain by mapping memory events and memory pointers based on the received activity data and associated data.

Figure 5:
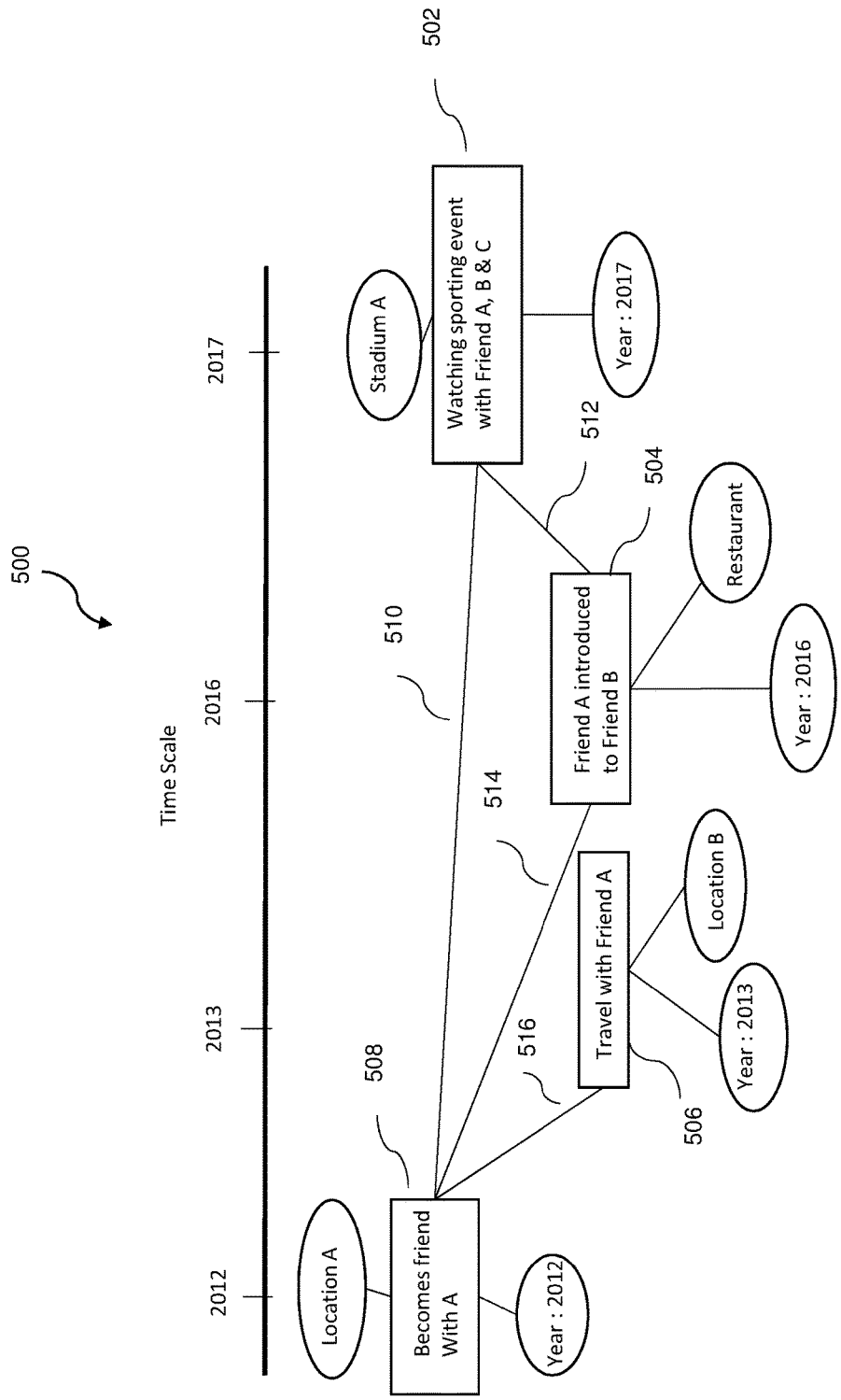
FIG. 5 depicts example memory chain graph in accordance with one or more embodiments of the present invention.

FIG. 5 depicts an example memory chain graph 500 that may be generated in accordance with one or more embodiments of the present invention. Memory chain graph 500 includes a plurality of memory events 502, 504, 506, 508 and a plurality of memory pointers 510, 512, 514, 516 spanning a plurality of time periods. Each memory event of the plurality of memory events 502, 504, 506, 508 is correlated with corresponding memory information, such as for example images captured by the user device at a certain event, audio captured at the certain event, and other types of information. In this example, memory chain graph 500 is generated based on activities that the user conducted with persons A, B, and C who are friends of the user. Memory event 502 pertains to an activity in which the user watched a sporting event with person A, B, and C. Memory event 502 is correlated with the year "2017" and the location "stadium A," which is when and where the user watched the sporting event. Memory event 504 pertains to an activity where the user is first introduced to person B. Memory event 504 is correlated with the year "2016" and the location "restaurant" which is when and where the user was first introduced to person B. Memory event 506 pertains to an activity in which the user traveled with person A, in which memory event 506 is correlated with the year "2013" and with the location "Location B" which is when and where the user and person A traveled to. Memory event 508 pertains to an activity where the user became friends with person A. Memory event 508 is correlated with the year "2012" and the location "Location A," which is when and where the user and person A first became friends.

In this example, the plurality of memory events 502, 504, 506, 508 are linked via the plurality of memory pointers 510, 512, 514, 516. In particular, memory pointer 512 links memory event 502 to memory event 504, memory pointer 514 links memory event 504 to memory event 508. Memory pointer 516 links memory event 506 to memory event 508. Although memory chain graph 500 is shown as including four memory events and four memory pointers, other numbers of memory events and/or pointers may be used depending on a variety of factors such as, for example, the number of types of activities that are being analyzed. In some embodiments of the present invention, memory chain graph 500 further includes nodes representing associated metadata, such as a location of a particular event, a time of a particular event, year of a particular event, or other types of associated metadata.

Referring back to FIG. 4, memory recall system 404 is configured to identify a memory event that the user is unable to presently recall (e.g., via memory recall detector component 410). In some embodiments of the present invention, memory recall system 404 is configured to receive at least one of biometric data or visual data pertaining to the user during the presentation of the information to the user and then to detect detecting whether the user is presently recalling the memory event by at least analyzing the at least one of biometric data or visual data and comparing a result of the analysis to a predetermined threshold. For example, in some embodiments of the present invention, memory recall system 404 presents the user with images of certain people while the heartrate of the user is monitored. If memory recall system 404 detects that the user's heartrate is elevated above a predetermined threshold (e.g., predetermined resting heart rate of the user, a standard heartrate for people of the same age of the user, etc.), memory recall system 404 then concludes that the user does not recognize a person that is presently being presented in images to the user. In some embodiments of the present invention, memory recall system 404 identifies a memory event that the user is unable to presently recall based on a specific input that is transmitted by the user or by a secondary user (e.g., a doctor of the user, a relative of the user, a friend of the user, etc.). In particular, in some embodiments of the present invention, a secondary user may inform memory recall system 404 of a particular memory event that the secondary user knows to have been forgotten by the user. For example, in some embodiments of the present invention, a relative of the user may identify that the user has forgotten who the relative is. The relative may then transmit a message to the memory recall system 404 to inform the system of what particular event has been forgotten by the user. The message may be transmitted by the secondary user to memory recall system 404 in various suitable ways such as, for example, transmitting an audio, video, or text message to memory recall system 404 from a separate device (e.g., user device 402 or another computing device). In some embodiments of the present invention, the message may be transmitted by the secondary user to the memory recall system 404 via an input interface of memory recall system 404. For example, in some embodiments of the present invention, the secondary user inputs the message via a keyboard, mouse, microphone, or other interface of memory recall system 404.

Memory recall system 404 is configured to select a memory pointer that is linked to the memory event that was identified as not being recalled by the user (e.g., via memory pointer selector component 412). Memory recall system 404 is configured to present the user with information corresponding to the selected memory pointer to assist the user in recalling the memory event. In particular, in some embodiments of the present invention, having identified a memory event that has not been recalled by the user (i.e. a first memory event), memory recall system 404 then selects the memory pointer by selecting between a second memory pointer and a third memory pointer, in which the second memory pointer links the first memory event to a second memory event, in which the third memory pointer links the first memory event to a third memory event.

In some embodiments of the present invention, the memory pointer is selected by memory recall system 404 based on the length of time that is associated with the memory pointers linked to the identified memory event. For example, in some embodiments of the present invention, memory recall system 404 is configured to select the memory pointer that points to the linked memory event that occurred most recently as compared to the other linked memory events. This may be useful in various scenarios such as, for example, when a user is experiencing long-term memory loss and is able to more easily recollect recent events as compared to events that occurred long ago. For example, in the context of memory graph 500 of FIG. 5, if memory recall system 404 identifies that memory event 502 (i.e., the first memory event) is not presently being recalled by the user (i.e. "Watching sporting event with Friend A, B & C"), in some embodiments of the present invention memory recall system 404 is configured to select memory pointer 512 over memory pointer 510 because memory pointer 512 is linked to memory event 504 which occurred more recently relative to memory event 502 as compared to memory event 508 (e.g., memory event 504 occurred subsequent to memory event 508, both of which occurred prior to memory event 502). In particular, in some embodiments of the present invention, memory recall system 404 is configured to select a second memory pointer if a second time period occurred subsequent to a third time period and to select a third memory pointer if a third time period occurred subsequent to the second time period, in which the memory event that has been identified as not being recalled by the user is linked to a second memory event via the second memory pointer and linked to a third memory event via the third memory pointer, in which the second memory event occurred during the second time period whereas the third memory event occurred during the third time period.

Similarly, in some embodiments of the present invention, memory recall system 404 is configured to select the memory pointer that points to the linked memory event that occurred earliest in time as compared to the other linked memory events. This may be useful in various scenarios such as, for example, when a user is experiencing short-term memory loss and is able to more easily recollect events that occurred a long time ago as compared to events that occurred recently. For, example, in the context of memory graph 500 of FIG. 5, if memory recall system 404 identifies that memory event 502 (i.e., the first memory event) is not presently being recalled by the user (i.e. "Watching sporting event with Friend A, B & C"), in some embodiments of the present invention memory recall system 404 is configured to select memory pointer 510 over memory pointer 512 (i.e., the first memory pointer) because memory pointer 512 is linked to memory event 504 which occurred more recently relative to memory event 502 as compared to memory event 508 (e.g., memory event 508 occurred prior to memory event 504, both of which occurred prior to memory event 502 memory). In particular, in some embodiments of the present invention, memory recall system 404 is configured to select the second memory pointer if the second time period occurred prior to the third time period and select the third memory pointer if the third time period occurred prior to the second time period.

Referring back to FIG. 4, memory recall system 404 is configured to present to the user information corresponding to the selected memory pointer to assist the user in recalling the memory event. In some embodiments of the present invention, presenting the user with information corresponding to the selected memory pointer includes presenting the user with at least one of images, text, video, or audio data that is associated with the selected memory pointer.

In some embodiments of the present invention, while the user is being presented with information corresponding to the selected memory pointer (e.g., second or third memory pointer) to assist in recollection of the identified lost memory event, memory recall system 404 is configured to again detect whether the user is presently recalling the identified memory event (i.e., the first memory event). In response to detecting if the user still does not recall the identified memory event, memory recall system 404 then selects an additional memory pointer (i.e., a fourth memory pointer) that is linked to the event that was pointed to by the last selected pointer and then presents the user with information corresponding to the additional memory pointer to further assist the user in recalling the lost memory event. For example, in the context of memory graph 500 of FIG. 5, if memory recall system 404 identifies that memory event 502 is not presently being recalled by the user and then provides the user with information corresponding to memory pointer 512 that is linked to memory event 504, in some embodiments of the present invention, memory recall system 404 then selects memory pointer 514, which links memory event 504 to memory event 508. Memory recall system 404 then presents the user with information corresponding to memory pointer 514. In particular, in some embodiment of the present invention, having selected the third memory pointer, for example, and having provided information to the user that is related to the third memory pointer, memory recall system 404 then selects a fourth memory pointer and presents the user with information corresponding to the fourth memory pointer to further assist the user in recalling the memory event, in which the second memory event is linked to the third memory event via the fourth memory pointer.

Figure 6:
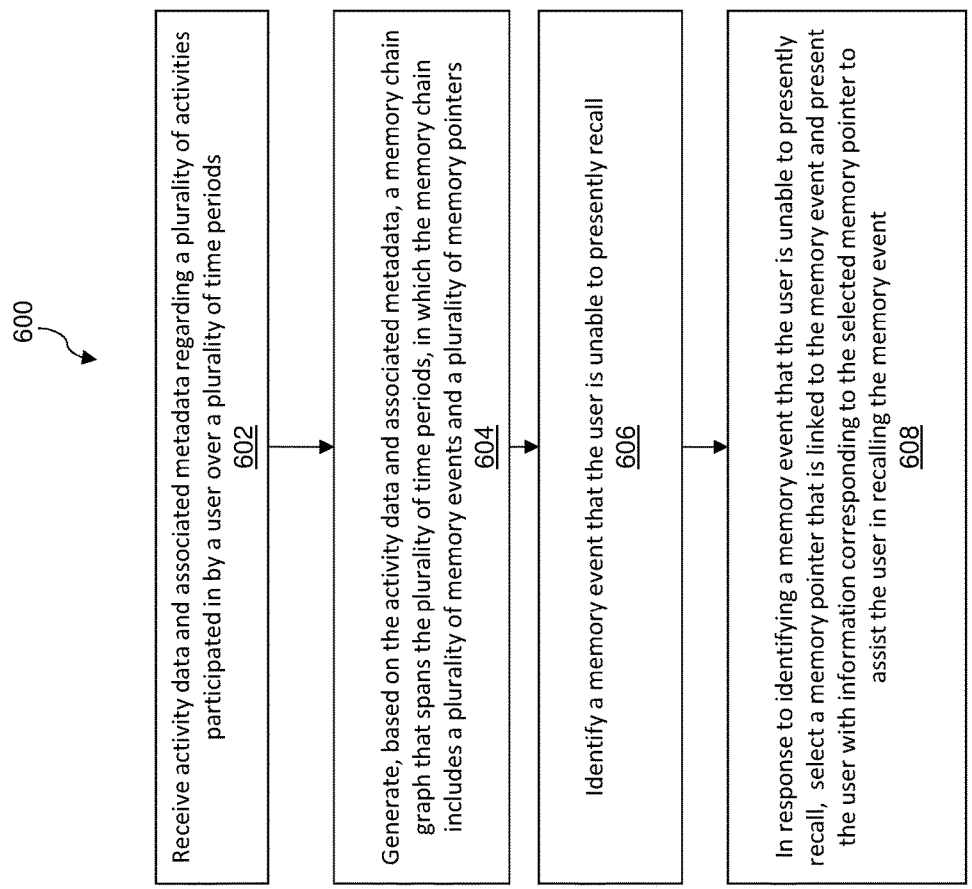
FIG. 6 depicts a flow diagram illustrating a methodology in accordance with one or more embodiments of the present invention.

Additional details of the operation of system 404 will now be described with reference to FIG. 6, wherein FIG. 6 depicts a flow diagram illustrating a methodology 600 according to one or more embodiments of the present invention. At 602, activity data and associated metadata regarding a plurality of activities participated in by a user over a plurality of time periods is received by the system. At 604, a memory chain that spans the plurality of time periods is generated by the system based on the received activity data and associated metadata. In some embodiments the memory chain is a memory chain graph. The memory chain includes a plurality of memory events and a plurality of memory pointers, in which each memory event of the plurality of memory events is linked to at least one other event of the plurality of events via a memory pointer of the plurality of memory pointers. At 606, a memory event that the user is unable to presently recall is identified by the system. At 608 pointer, in response to identifying a memory event that the user is unable to presently recall, a memory pointer that is linked to the memory event is selected by the system and then the user is presented with information corresponding to the selected memory pointer to assist the user in recalling the memory event.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer-implemented method for assisting recall of a lost memory, the method comprising:

receiving, by a memory recall system comprising one or more processors, activity data and associated metadata regarding a plurality of activities participated in by a user over a plurality of time periods;

generating, by a memory chain graphing component of the memory recall system, a memory chain graph that spans the plurality of time periods, wherein the memory chain graph is generated based on the activity data and associated metadata, wherein the memory chain graph includes a plurality of memory events and a plurality of memory pointers, wherein each memory event of the plurality of memory events is linked to at least one other event of the plurality of events via a memory pointer of the plurality of memory pointers;

identifying, by the memory recall system, a memory event of the memory chain graph that the user is unable to presently recall; and in response to identifying the memory event that the user is unable to presently recall:

selecting, by the memory recall system, a memory pointer of the plurality of memory pointers that is linked to the memory event;

presenting the user with information corresponding to the selected memory pointer to assist the user in recalling the memory event, the presenting comprising outputting the information corresponding to the selected memory pointer to the user via a user device of the user;

collecting, by the memory recall system, biometric data pertaining to the user during the presenting, the biometric data obtained from one or more sensors; and analyzing, by a memory recall detector component of the memory recall system, the biometric data to determine whether the user recalled the memory event.

2. The computer-implemented method of claim 1, wherein the memory event is linked to a second memory event via a second memory pointer and linked to a third memory event via a third memory pointer, wherein selecting the memory pointer comprises selecting the second memory pointer or the third memory pointer.

3. The computer-implemented method of claim 2, wherein the second memory event occurred during a second time period of the plurality of time periods, wherein the third memory event occurred during a third time period of the plurality of time periods, wherein selecting the second memory pointer or the third memory pointer comprises:

selecting the second memory pointer if the second time period occurred prior to the third time period; and selecting the third memory pointer if the third time period occurred prior to the second time period.

4. The computer-implemented method of claim 2, wherein the second memory event occurred during a second time period of the plurality of time periods, wherein the third memory event occurred during a third time period of the plurality of time periods, wherein selecting the second memory pointer or the third memory pointer comprises:

selecting the second memory pointer if the second time period occurred subsequent to the third time period; and selecting the third memory pointer if the third time period occurred subsequent to the second time period.

5. The computer-implemented method of claim 1, wherein the memory event is linked to a second memory event via a second memory pointer and to a third memory event via a third memory pointer, wherein the second memory event is linked to the third memory event via a fourth memory pointer, wherein the second memory event occurred during a second time period of the plurality of time periods, wherein the third memory event occurred during a third time period of the plurality of time periods, wherein the third time period occurred subsequent to the second time period, wherein selecting the memory pointer comprises selecting the third memory pointer, wherein the method further comprises:

in response to detecting the user still does not recall the memory event, selecting the fourth memory pointer and presenting the user with information corresponding to the fourth memory pointer to further assist the user in recalling the memory event.

6. The computer-implemented method of claim 1, wherein presenting the user with information corresponding to the selected memory pointer includes presenting the user with at least one of images, text, video, or audio data that is associated with the selected memory pointer.

7. A computer program product for assisting recall of a lost memory, the computer program product comprising a computer readable storage medium having program instructions embodied therewith, the program instructions executable by a memory recall system comprising one or more processors to cause the memory recall system to perform a method, the method comprising:

receiving, by the memory recall system, activity data and associated metadata regarding a plurality of activities participated in by a user over a plurality of time periods;

generating, by a memory chain graphing component of the memory recall system, a memory chain graph that spans the plurality of time periods, wherein the memory chain graph is generated based on the activity data and associated metadata, wherein the memory chain graph includes a plurality of memory events and a plurality of memory pointers, wherein each memory event of the plurality of memory events is linked to at least one other event of the plurality of events via a memory pointer of the plurality of memory pointers;

identifying, by the memory recall system, a memory event of the memory chain graph that the user is unable to presently recall; and in response to identifying the memory event that the user is unable to presently recall:

selecting, by the memory recall system, a memory pointer of the plurality of memory pointers that is linked to the memory event;

presenting the user with information corresponding to the selected memory pointer to assist the user in recalling the memory event, the presenting comprising outputting the information corresponding to the selected memory pointer to the user via a user device of the user;

collecting, by the memory recall system, biometric data pertaining to the user during the presenting, the biometric data obtained from one or more sensors; and analyzing, by a memory recall detector component of the memory recall system, the biometric data to determine whether the user recalled the memory event.

8. The computer program product of claim 7, wherein the memory event is linked to a second memory event via a second memory pointer and linked to a third memory event via a third memory pointer, wherein selecting the memory pointer comprises selecting the second memory pointer or the third memory pointer.

9. The computer program product of claim 8, wherein the second memory event occurred during a second time period of the plurality of time periods, wherein the third memory event occurred during a third time period of the plurality of time periods, wherein selecting the second memory pointer or the third memory pointer comprises:

selecting the second memory pointer if the second time period occurred prior to the third time period; and selecting the third memory pointer if the third time period occurred prior to the second time period.

10. The computer program product of claim 8, wherein the second memory event occurred during a second time period of the plurality of time periods, wherein the third memory event occurred during a third time period of the plurality of time periods, wherein selecting the second memory pointer or the third memory pointer comprises:

selecting the second memory pointer if the second time period occurred subsequent to the third time period; and selecting the third memory pointer if the third time period occurred subsequent to the second time period.

11. The computer program product of claim 7, wherein the memory event is linked to a second memory event via a second memory pointer and to a third memory event via a third memory pointer, wherein the second memory event is linked to the third memory event via a fourth memory pointer, wherein the second memory event occurred during a second time period of the plurality of time periods, wherein the third memory event occurred during a third time period of the plurality of time periods, wherein the third time period occurred subsequent to the second time period, wherein selecting the memory pointer comprises selecting the third memory pointer, wherein the method further comprises:

in response to detecting the user still does not recall the memory event, selecting the fourth memory pointer and presenting the user with information corresponding to the fourth memory pointer to further assist the user in recalling the memory event.

12. The computer program product of claim 7, wherein presenting the user with information corresponding to the selected memory pointer includes presenting the user with at least one of images, text, video, or audio data that is associated with the selected memory pointer.

13. A memory recall system for assisting recall of a lost memory, the memory recall system comprising one or more processors configured to perform a method, the method comprising:

receiving, by the memory recall system, activity data and associated metadata regarding a plurality of activities participated in by a user over a plurality of time periods;

generating, by a memory chain graphing component of the memory recall system, a memory chain graph that spans the plurality of time periods, wherein the memory chain graph is generated based on the activity data and associated metadata, wherein the memory chain graph includes a plurality of memory events and a plurality of memory pointers, wherein each memory event of the plurality of memory events is linked to at least one other event of the plurality of events via a memory pointer of the plurality of memory pointers;

identifying, by the memory recall system, a memory event of the memory chain graph that the user is unable to presently recall; and in response to identifying the memory event that the user is unable to presently recall:

selecting, by the memory recall system, a memory pointer of the plurality of memory pointers that is linked to the memory event;

presenting the user with information corresponding to the selected memory pointer to assist the user in recalling the memory event, the presenting comprising outputting the information corresponding to the selected memory pointer to the user via a user device of the user;

collecting, by the memory recall system, biometric data pertaining to the user during the presenting, the biometric data obtained from one or more sensors; and analyzing, by a memory recall detector component of the memory recall system, the biometric data to determine whether the user recalled the memory event.

14. The system of claim 13, wherein the memory event is linked to a second memory event via a second memory pointer and linked to a third memory event via a third memory pointer, wherein selecting the memory pointer comprises selecting the second memory pointer or the third memory pointer.

15. The system of claim 14, wherein the second memory event occurred during a second time period of the plurality of time periods, wherein the third memory event occurred during a third time period of the plurality of time periods, wherein selecting the second memory pointer or the third memory pointer comprises:

selecting the second memory pointer if the second time period occurred prior to the third time period; and selecting the third memory pointer if the third time period occurred prior to the second time period.

16. The system of claim 14, wherein the second memory event occurred during a second time period of the plurality of time periods, wherein the third memory event occurred during a third time period of the plurality of time periods, wherein selecting the second memory pointer or the third memory pointer comprises:

selecting the second memory pointer if the second time period occurred subsequent to the third time period; and selecting the third memory pointer if the third time period occurred subsequent to the second time period.

17. The system of claim 13, wherein the memory event is linked to a second memory event via a second memory pointer and to a third memory event via a third memory pointer, wherein the second memory event is linked to the third memory event via a fourth memory pointer, wherein the second memory event occurred during a second time period of the plurality of time periods, wherein the third memory event occurred during a third time period of the plurality of time periods, wherein the third time period occurred subsequent to the second time period, wherein selecting the memory pointer comprises selecting the third memory pointer, wherein the method further comprises:

in response to detecting the user still does not recall the memory event, selecting the fourth memory pointer and presenting the user with information corresponding to the fourth memory pointer to further assist the user in recalling the memory event.

\* \* \* \* \*